US009615969B2

(12) United States Patent
Nissan et al.

(10) Patent No.: US 9,615,969 B2
(45) Date of Patent: Apr. 11, 2017

(54) MULTI-PORT VITRECTOMY PROBE WITH DUAL CUTTING EDGES

(71) Applicant: Alcon Research, Ltd., Fort Worth, TX (US)

(72) Inventors: Oded M. Nissan, Houston, TX (US); Dana Tendler, Tel Aviv (IL)

(73) Assignee: Novartis AG, Basel (CH)

( * ) Notice: Subject to any disclaimer, the term of this patent is extended or adjusted under 35 U.S.C. 154(b) by 338 days.

(21) Appl. No.: 14/103,903

(22) Filed: Dec. 12, 2013

(65) Prior Publication Data

US 2014/0171997 A1   Jun. 19, 2014

Related U.S. Application Data

(60) Provisional application No. 61/738,509, filed on Dec. 18, 2012.

(51) Int. Cl.
*A61B 17/32* (2006.01)
*A61F 9/007* (2006.01)
*A61B 17/00* (2006.01)

(52) U.S. Cl.
CPC ..... *A61F 9/00763* (2013.01); *A61B 2017/00544* (2013.01)

(58) Field of Classification Search
CPC ............. A61F 9/00763; A61F 9/00736; A61B 17/32002; A61B 2017/320028
See application file for complete search history.

(56) References Cited

U.S. PATENT DOCUMENTS

| 3,618,594 | A |   | 11/1971 | Banko |
|---|---|---|---|---|
| 3,736,938 | A |   | 6/1973 | Evvard et al. |
| 3,815,604 | A |   | 6/1974 | O'Malley et al. |
| 3,906,954 | A |   | 9/1975 | Baehr et al. |
| 3,941,122 | A |   | 3/1976 | Jones |
| 3,982,541 | A |   | 9/1976 | L'Esperance, Jr. |
| 4,011,869 | A | * | 3/1977 | Seiler, Jr. ............ A61F 9/00763 604/22 |
| 4,014,342 | A |   | 3/1977 | Staub et al. |
| 4,099,529 | A |   | 7/1978 | Peyman |
| 4,111,207 | A |   | 9/1978 | Seiler, Jr. |
| 4,210,146 | A |   | 7/1980 | Banko |
| 4,428,748 | A |   | 1/1984 | Peyman et al. |

(Continued)

FOREIGN PATENT DOCUMENTS

BR   PI 1005732 A2   4/2013
CH       704384 A2   7/2012
(Continued)

*Primary Examiner* — Julie A Szpira (57) ABSTRACT

A vitrectomy probe includes a hand-graspable body and an external tube extending from the hand-graspable body and sized to penetrate an eye of a patient during an ocular surgery. In an aspect, the external tube includes a closed end and a plurality of ports sized to receive vitreous material. In another aspect, an internal tube has a first cutting edge facing in a proximal direction and a second cutting edge facing in a distal direction. The first cutting edge oscillates across the port of the external tube to cut tissue in the port with the first cutting edge when the internal tube moves in the proximal direction and to cut tissue in the port with the second cutting edge when the internal tube moves in the distal direction.

6 Claims, 6 Drawing Sheets

(56) References Cited

U.S. PATENT DOCUMENTS

| | | | |
|---|---|---|---|
| 4,513,745 A * | 4/1985 | Amoils | A61F 9/00763 604/22 |
| 4,525,842 A | 6/1985 | Myers | |
| 4,577,629 A | 3/1986 | Martinez | |
| 4,583,539 A | 4/1986 | Karlin et al. | |
| 4,655,743 A | 4/1987 | Hyde | |
| 4,671,273 A | 6/1987 | Lindsey | |
| 4,694,828 A | 9/1987 | Eichenbaum | |
| 4,696,298 A | 9/1987 | Higgins et al. | |
| 4,811,734 A * | 3/1989 | McGurk-Burleson | A61B 17/32002 30/240 |
| 4,846,172 A | 7/1989 | Berlin | |
| 4,909,249 A | 3/1990 | Akkas et al. | |
| 4,940,468 A | 7/1990 | Petillo | |
| 4,963,142 A | 10/1990 | Loertscher | |
| 5,019,035 A | 5/1991 | Missirlian et al. | |
| 5,047,008 A | 9/1991 | de Juan, Jr. et al. | |
| 5,106,364 A * | 4/1992 | Hayafuji | A61B 17/32002 30/208 |
| 5,176,628 A | 1/1993 | Charles et al. | |
| 5,226,910 A | 7/1993 | Kajiyama et al. | |
| 5,275,607 A | 1/1994 | Lo et al. | |
| 5,284,472 A | 2/1994 | Sussman et al. | |
| 5,285,795 A | 2/1994 | Ryan et al. | |
| 5,423,844 A | 6/1995 | Miller | |
| 5,458,112 A * | 10/1995 | Weaver | A61B 10/0275 600/566 |
| 5,474,532 A * | 12/1995 | Steppe | A61F 9/00763 604/22 |
| 5,547,473 A | 8/1996 | Peyman | |
| 5,630,827 A * | 5/1997 | Vijfvinkel | A61B 10/0266 604/22 |
| 5,688,264 A | 11/1997 | Ren et al. | |
| 5,720,760 A | 2/1998 | Becker et al. | |
| 5,772,627 A | 6/1998 | Acosta et al. | |
| 5,782,849 A | 7/1998 | Miller | |
| 5,788,667 A | 8/1998 | Stoller | |
| 5,843,111 A * | 12/1998 | Vijfvinkel | A61B 10/0266 604/22 |
| 5,980,546 A * | 11/1999 | Hood | A61B 17/32001 604/22 |
| 5,984,916 A | 11/1999 | Lai | |
| 6,004,284 A | 12/1999 | Sussman et al. | |
| 6,024,751 A | 2/2000 | Lovato et al. | |
| 6,027,493 A | 2/2000 | Donitzky et al. | |
| 6,156,049 A | 12/2000 | Lovato et al. | |
| 6,258,111 B1 | 7/2001 | Ross et al. | |
| 6,270,471 B1 | 8/2001 | Hechel et al. | |
| 6,325,792 B1 | 12/2001 | Swinger et al. | |
| 6,352,535 B1 | 3/2002 | Lewis et al. | |
| 6,383,203 B1 | 5/2002 | Makihara | |
| 6,485,499 B1 | 11/2002 | Oberkamp et al. | |
| 6,514,268 B2 | 2/2003 | Finlay et al. | |
| 6,575,990 B1 | 6/2003 | Wang et al. | |
| 6,695,821 B1 * | 2/2004 | Sjaarda | A61M 3/0279 604/264 |
| 6,709,408 B2 | 3/2004 | Fisher | |
| 6,743,245 B2 | 6/2004 | Lobdell | |
| 6,758,824 B1 | 7/2004 | Miller et al. | |
| 6,773,445 B2 | 8/2004 | Finlay et al. | |
| 6,872,185 B2 | 3/2005 | Fisher | |
| 6,875,221 B2 | 4/2005 | Cull | |
| 6,890,309 B2 | 5/2005 | Fisher | |
| 6,908,440 B2 | 6/2005 | Fisher | |
| 7,070,604 B1 | 7/2006 | Garito et al. | |
| 7,285,107 B1 | 10/2007 | Charles | |
| 7,335,217 B2 | 2/2008 | Wang et al. | |
| 7,600,405 B2 | 10/2009 | Maurer, Jr. et al. | |
| 8,038,692 B2 | 10/2011 | Valencia et al. | |
| 8,172,865 B2 | 5/2012 | DeBoer et al. | |
| 8,187,293 B2 | 5/2012 | Kirchhevel | |
| 8,298,253 B2 | 10/2012 | Charles | |
| 8,313,501 B2 | 11/2012 | Miller et al. | |
| 8,328,835 B2 | 12/2012 | Perkins et al. | |
| 8,545,528 B2 | 10/2013 | Rob et al. | |
| 8,608,753 B2 | 12/2013 | Luloh et al. | |
| 8,641,701 B2 | 2/2014 | Hangai et al. | |
| 8,728,108 B2 | 5/2014 | Gao et al. | |
| 8,808,318 B2 | 8/2014 | Auld et al. | |
| 8,818,564 B2 | 8/2014 | Zhou et al. | |
| 8,821,524 B2 | 9/2014 | Agahi | |
| 8,979,867 B2 | 3/2015 | Peyman | |
| 9,060,841 B2 | 6/2015 | McCawley | |
| 9,101,442 B2 | 8/2015 | McDonell | |
| 9,211,608 B2 | 12/2015 | Chen et al. | |
| 9,216,067 B2 | 12/2015 | Peyman | |
| 2003/0032895 A1 | 2/2003 | Fisher | |
| 2003/0114870 A1 | 6/2003 | Cull | |
| 2003/0195538 A1 | 10/2003 | Wang et al. | |
| 2004/0049217 A1 | 3/2004 | Ross et al. | |
| 2004/0133190 A1 | 7/2004 | Hobart et al. | |
| 2005/0090765 A1 | 4/2005 | Fisher | |
| 2005/0154379 A1 | 7/2005 | McGowan, Sr. et al. | |
| 2005/0187537 A1 | 8/2005 | Loeb et al. | |
| 2005/0209618 A1 | 9/2005 | Auld | |
| 2006/0004397 A1 | 1/2006 | Osawa | |
| 2006/0161145 A1 | 7/2006 | Lin et al. | |
| 2006/0271082 A1 | 11/2006 | Kirchhevel et al. | |
| 2007/0088376 A1 | 4/2007 | Zacharias | |
| 2007/0129732 A1 | 6/2007 | Zacharias | |
| 2007/0173870 A2 | 7/2007 | Zacharias | |
| 2007/0185514 A1 | 8/2007 | Kirchhevel | |
| 2007/0255196 A1 | 11/2007 | Wuchinich | |
| 2008/0154292 A1 | 6/2008 | Huculak et al. | |
| 2008/0172077 A1 | 7/2008 | Valencia et al. | |
| 2008/0172078 A1 | 7/2008 | Svetic | |
| 2008/0188881 A1 | 8/2008 | Chon | |
| 2008/0208233 A1 | 8/2008 | Barnes et al. | |
| 2009/0069831 A1 | 3/2009 | Miller et al. | |
| 2009/0088784 A1 | 4/2009 | DeBoer et al. | |
| 2009/0157111 A1 | 6/2009 | Goh et al. | |
| 2009/0259242 A1 | 10/2009 | Gerg et al. | |
| 2009/0281479 A1 | 11/2009 | Gagnepain et al. | |
| 2010/0042125 A1 | 2/2010 | Maurer, Jr. et al. | |
| 2010/0106054 A1 | 4/2010 | Hangai et al. | |
| 2010/0152762 A1 | 6/2010 | Mark | |
| 2010/0305596 A1 | 12/2010 | Peterson et al. | |
| 2010/0312169 A1 | 12/2010 | Auld et al. | |
| 2011/0144641 A1 | 6/2011 | Dimalanta, Jr. et al. | |
| 2011/0190690 A1 | 8/2011 | Humayun et al. | |
| 2011/0295292 A1 | 12/2011 | Hsia | |
| 2011/0295296 A1 | 12/2011 | Charles | |
| 2012/0083793 A1 | 4/2012 | Foster | |
| 2012/0158030 A1 | 6/2012 | Underwood et al. | |
| 2012/0221033 A1 | 8/2012 | Auld et al. | |
| 2013/0053759 A1 | 2/2013 | McCawley | |
| 2013/0079806 A1 | 3/2013 | Peyman | |
| 2013/0090635 A1 | 4/2013 | Mansour | |
| 2013/0110147 A1 | 5/2013 | Dame | |
| 2013/0150875 A1 | 6/2013 | McDonell et al. | |
| 2013/0211439 A1 * | 8/2013 | Geuder | A61B 17/32002 606/171 |
| 2013/0325044 A1 | 12/2013 | Wang et al. | |
| 2014/0074013 A1 | 3/2014 | McCary et al. | |
| 2014/0171994 A1 | 6/2014 | Lee et al. | |
| 2014/0171995 A1 | 6/2014 | McDonell | |
| 2014/0171996 A1 | 6/2014 | McDonell et al. | |
| 2014/0171997 A1 | 6/2014 | Nissan et al. | |
| 2014/0296900 A1 | 10/2014 | Barnes et al. | |
| 2014/0364885 A1 | 12/2014 | Wells et al. | |
| 2015/0157503 A1 | 6/2015 | Chon | |
| 2015/0182379 A1 | 7/2015 | Fantoni et al. | |
| 2015/0282987 A1 | 10/2015 | McDonell | |
| 2015/0306286 A1 | 10/2015 | Ross et al. | |
| 2015/0335485 A1 | 11/2015 | Rieger et al. | |
| 2015/0342678 A1 | 12/2015 | Deladurantaye et al. | |
| 2016/0022489 A1 | 1/2016 | Hartstra | |
| 2016/0120697 A1 | 5/2016 | Farley | |

(56) References Cited

U.S. PATENT DOCUMENTS

2016/0128870 A1    5/2016   McDonell
2016/0135991 A1    5/2016   Farley et al.

FOREIGN PATENT DOCUMENTS

| | | |
|---|---|---|
| DE | 20022265 U1 | 7/2000 |
| DE | 10032007 A1 | 1/2002 |
| DE | 102010050337 A1 | 5/2012 |
| DE | 202013012000 U1 | 2/2015 |
| DE | 102013201784 B4 | 5/2015 |
| EP | 0919210 A1 | 6/1999 |
| EP | 1542592 A1 | 6/2005 |
| EP | 2 521 518 | 11/2012 |
| EP | 2802303 A1 | 11/2014 |
| EP | 2 863 853 | 4/2015 |
| EP | 2 913 034 A1 | 9/2015 |
| EP | 2 967 991 A1 | 1/2016 |
| GB | 2004754 A | 4/1979 |
| GB | 2167305 B | 11/1988 |
| NL | 1034654 C2 | 5/2009 |
| WO | WO 94/09711 A1 | 5/1994 |
| WO | WO 94/09849 A1 | 5/1994 |
| WO | WO 98/46147 A1 | 10/1998 |
| WO | WO 98/52502 | 11/1998 |
| WO | WO 00/47116 A1 | 8/2000 |
| WO | WO 00/78371 A1 | 12/2000 |
| WO | WO 01/30281 A1 | 5/2001 |
| WO | WO 2004/026142 A1 | 4/2004 |
| WO | WO 2010/096139 A2 | 8/2010 |
| WO | WO 2012/059092 A1 | 5/2012 |
| WO | WO 2012/083402 A1 | 6/2012 |
| WO | WO 2012/125674 A1 | 9/2012 |
| WO | WO 2013/009576 A1 | 1/2013 |
| WO | WO 2013/019859 A1 | 2/2013 |
| WO | WO 2013/043455 A1 | 3/2013 |
| WO | WO 2013/180718 A1 | 12/2013 |
| WO | WO 2014/002040 A1 | 1/2014 |
| WO | WO 2014/117774 A1 | 8/2014 |
| WO | WO 2014/142663 A1 | 9/2014 |
| WO | WO 2015/143308 A1 | 9/2015 |
| WO | WO 2015/158438 A1 | 10/2015 |
| WO | WO 2016/081133 A1 | 5/2016 |

\* cited by examiner

MULTI-PORT VITRECTOMY PROBE WITH DUAL CUTTING EDGES

PRIORITY CLAIM

This application claims the benefit of priority of U.S. Provisional Patent Application Ser. No. 61/738,509 titled "MULTI-PORT VITRECTOMY PROBE WITH DUAL CUTTING EDGES," filed on Dec. 18, 2012, whose inventors are Oded M. Nissan and Dana Tendler, which is hereby incorporated by reference in its entirety as though fully and completely set forth herein.

BACKGROUND

The present invention pertains to vitrectomy probes, systems, and methods. More particularly, but not by way of limitation, the present invention pertains to vitrectomy probes, systems, and methods utilizing a multi-port member or a dual cutting edge design.

Microsurgical procedures frequently require precision cutting and/or removing various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. These cutting probes typically include a hollow outer cutting member, a hollow inner cutting member arranged coaxially with and movably disposed within the hollow outer cutting member, and a port extending radially through the outer cutting member near the distal end thereof. Vitreous humor and/or membranes are aspirated into the open port, and the inner member is actuated, closing the port. Upon the closing of the port, cutting surfaces on both the inner and outer cutting members cooperate to cut the vitreous and/or membranes, and the cut tissue is then aspirated away through the inner cutting member.

While the conventional design is suitable for many applications, increases in cutting rate or in aspiration rate may increase efficiency of the surgical procedures, providing benefits to both the patients and the surgeon.

The present disclosure is directed to addressing one or more of the deficiencies in the prior art.

SUMMARY

In an exemplary aspect, the present disclosure is directed to a vitrectomy probe including a hand-graspable body and an external tube extending from the hand-graspable body and sized to penetrate an eye of a patient during an ocular surgery. The external tube may include a closed end and a port sized to receive vitreous material. The vitrectomy probe also includes an internal tube having a first cutting edge facing in a proximal direction and a second cutting edge facing in a distal direction. The internal tube may be disposed within the external tube so that the first cutting edge oscillates across the port of the external tube to cut tissue in the port with the first cutting edge when the internal tube moves in the proximal direction and to cut tissue in the port with the second cutting edge when the internal tube moves in the distal direction. A motor drives the internal tube in a reciprocating motion relative to the external tube.

In an aspect, the external tube comprises a plurality of ports. In an aspect, the plurality of ports is disposed at the distal end of the external tube and is evenly spaced about the circumference of the external tube. In an aspect, the internal tube comprises a distal portion and a proximal portion, where the distal portion comprises the first cutting edge facing the proximal portion and comprises the second cutting edge facing in the distal direction. In an aspect, the distal portion is rigidly fixed to and spaced apart from the proximal portion by an extending shaft.

In another exemplary aspect, the present disclosure is directed to a vitrectomy probe including a hand-graspable body and an external tube extending from the body and sized to penetrate an eye of a patient, the external tube having a closed end, the external tube having a plurality of ports sized to receive vitreous of an eye. An internal tube may be disposed within and axially slidable relative to the external tube. The internal tube may have a first cutting edge facing in a distal direction, and may be disposed within the external tube so that the first cutting edge oscillates across the port of the external tube to cut tissue in the plurality of ports with the first cutting edge when the internal tube moves in the distal direction. A motor may drive the internal tube in a reciprocating motion.

In an aspect, the internal tube includes a second cutting edge facing in a proximal direction, the internal tube being disposed within the external tube so that the second cutting edge oscillates across the port of the external tube to cut tissue in the port with the second cutting edge when the internal tube moves in the proximal direction. In an aspect, the internal tube comprises a distal portion and a proximal portion, the distal portion comprising the first cutting edge facing the distal direction and comprising the second cutting edge facing in the proximal direction.

In another exemplary aspect, the present disclosure is directed to a method of cutting vitreous with a vitrectomy probe. The method may include axially sliding an internal cutting tube within an external cutting tube in a proximal direction to cut vitreous with a proximally facing cutting edge on the internal cutting tube, axially sliding the internal cutting tube within the external cutting tube in a distal direction to cut vitreous with a distally facing cutting edge on the internal cutting tube, and aspirating the cut vitreous through the internal cutting tube.

In an aspect, the method includes cutting the vitreous with cross-blades extending across a first open distal end of a distal portion of the internal cutting tube, and aspirating the vitreous past cross-blades extending across a second open distal end of a proximal portion of the internal cutting tube. In an aspect, the method may include receiving vitreous into a plurality of ports of the external cutting tube for cutting by the internal cutting tube. In an aspect the method may include pulling a distal portion of the internal cutting tube in the proximal direction with a central bar extending between the distal portion of the internal cutting tube and a proximal portion of the internal cutting tube.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure is directed to surgical devices, systems, and methods for performing ophthalmic surgeries. The devices, systems, and methods are arranged and configured to increase a cut rate and/or an aspiration rate during a vitrectomy procedure. To accomplish this, the system incorporates a cutter that includes multiple outer ports and includes a cutter that cuts in both directions during a cutting cycle. This may result in shorter surgeries overall and may result in faster cut rates and aspiration rates that may lead to decreased traction in the vitreous.

Figure 1:
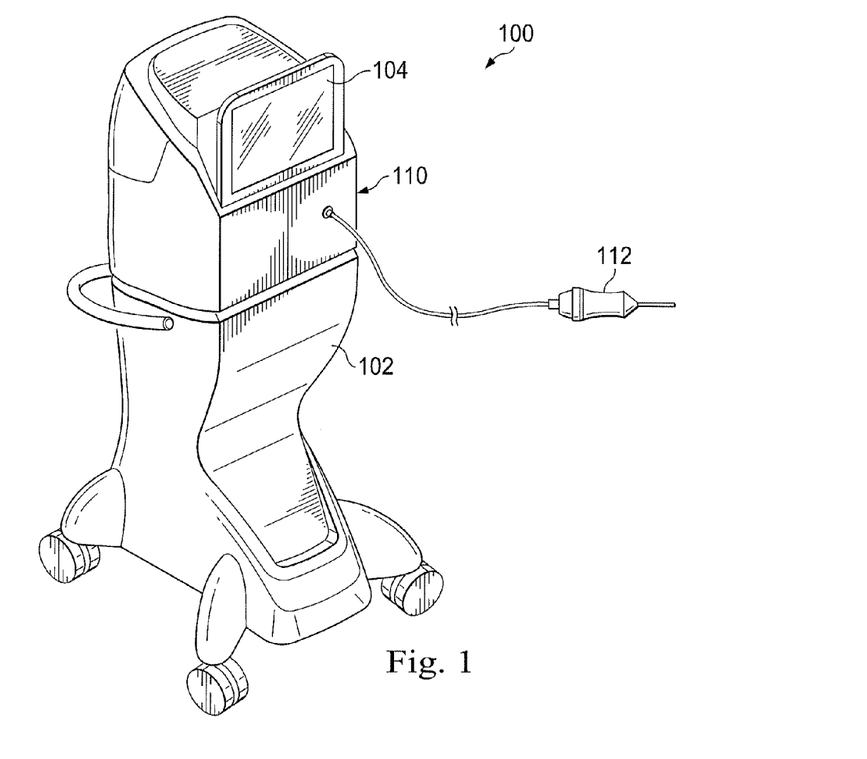
FIG. 1 is an illustration of an exemplary surgical system according to one aspect of the present disclosure consistent with the principles and teachings described herein.

FIG. 1 illustrates a vitrectomy surgical system, generally designated 100, according to an exemplary embodiment. The surgical system 100 includes a base housing 102 and an associated display screen 104 showing data relating to system operation and performance during a vitrectomy surgical procedure. The surgical system 100 includes a vitrectomy probe system 110 that includes a vitrectomy probe 112.

Figure 2:
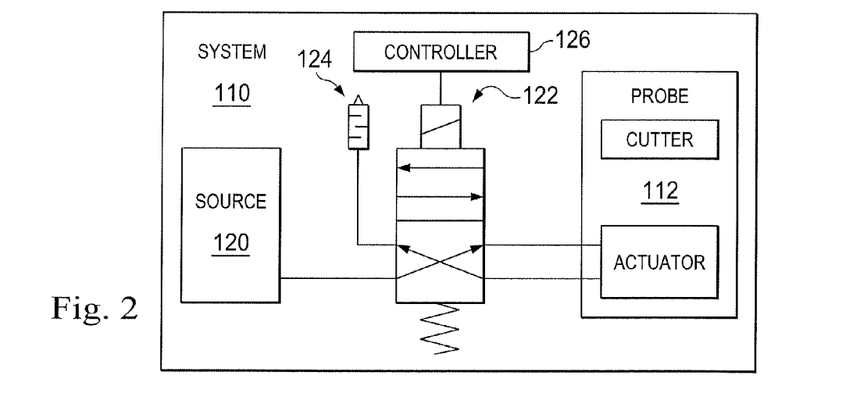
FIG. 2 is a box diagram of aspects of the exemplary surgical system of FIG. 1 according to one aspect described herein.

FIG. 2 is a schematic of the vitrectomy probe system 110. The probe system 110 includes the vitrectomy probe 112, a pneumatic pressure source 120, a probe driver shown as an adjustable directional on-off pneumatic driver 122, a muffler 124, and a controller 126. As can be seen, the source 120, the driver 122, the muffler 124, and the probe 112 are in fluid communication with each other along lines representing flow paths or flow lines. The controller 126 is in electrical communication with the driver 122.

Figure 3:
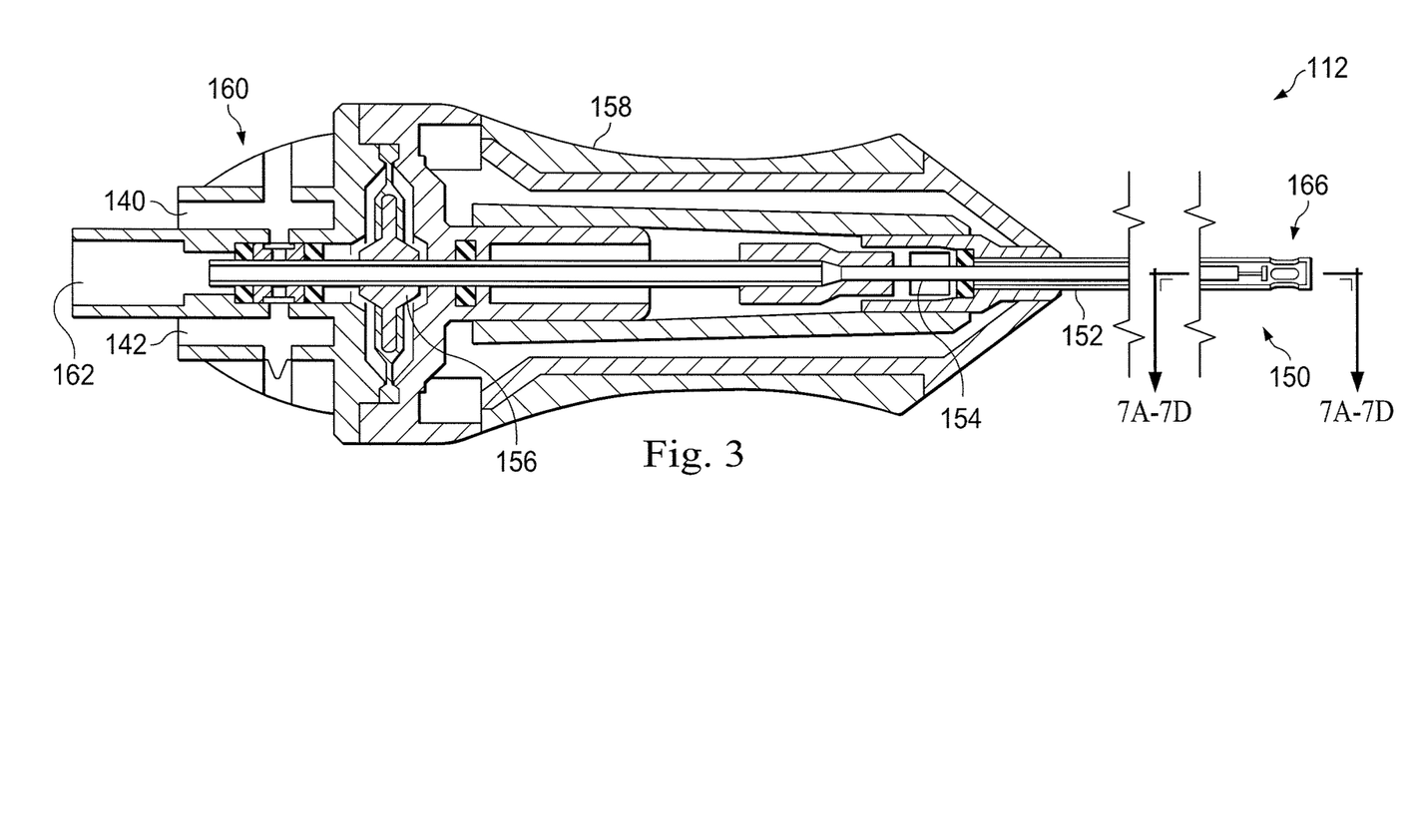
FIG. 3 is an illustration of an exemplary vitrectomy probe in cross-section operable in accordance with the principles and teachings described herein.

FIG. 3 shows a cross-sectional illustration of an exemplary vitrectomy probe, referenced by the numeral 112. In this example, the vitrectomy probe 112 is a pneumatically driven probe that operates by receiving pneumatic pressure alternating through first and second ports 140 and 142. The probe 112 includes as its basic components a cutter 150 comprising an outer cutting tube 152, an inner cutting tube 154, and a probe actuator or motor shown here as a reciprocating air driven diaphragm 156, all partially encased by a housing 158. The housing 158 includes an end piece 160 at the probe proximal end with the first and second air supply ports 140, 142 and one suction port 162.

Figure 4:
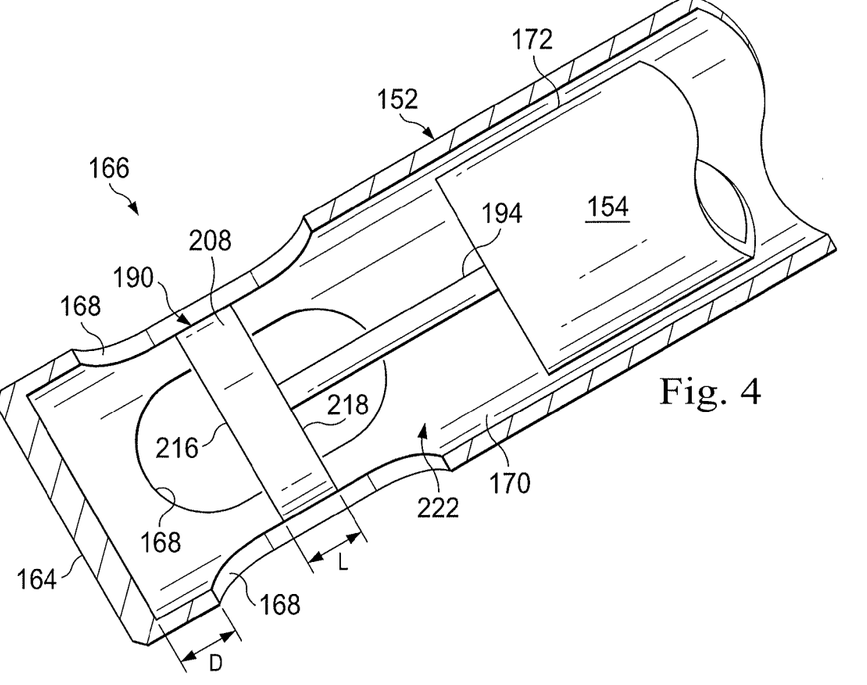
FIG. 4 is an illustration of an exemplary distal end of the vitrectomy probe in partial cross-section consistent with the principles and teachings described herein.
Figure 5:
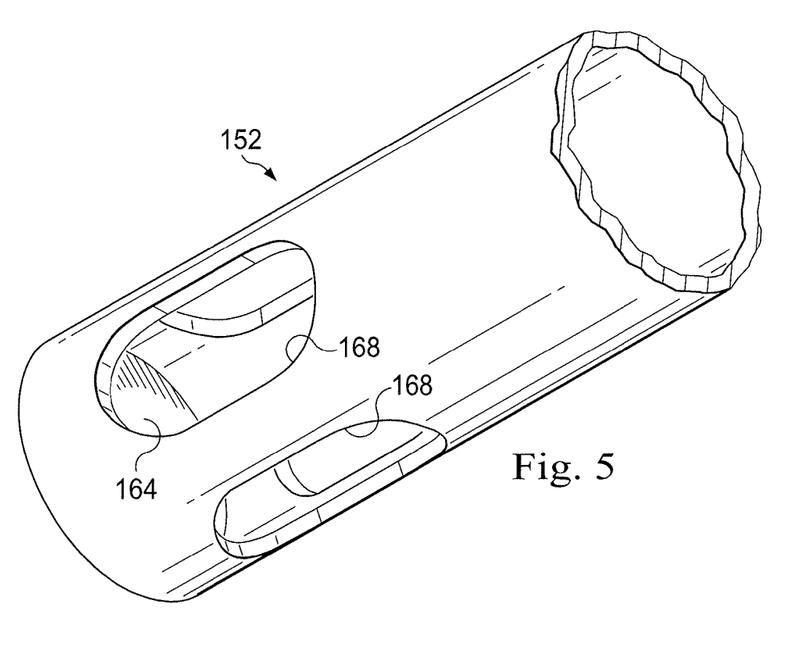
FIG. 5 is an illustration of an exemplary outer cutting tube consistent with the principles and teachings described herein.

As can be seen, the cutter 150 extends from the housing 158 and includes a distal end 166. FIG. 4 shows the distal end 166 of the cutting tube 150 in greater detail. It is a partial cross-sectional view showing the outer cutting tube 152 in cross-section and showing the inner cutting tube 154 in place in the outer cutting tube 152. Referring to FIG. 4, the inner cutting tube 154 fits within the outer cutting tube 152 in a coaxial manner, and the inner tube is axially moveable relative to the outer cutting tube. FIG. 5 shows the distal end of the outer cutting tube 152 in an isometric view.

Referring to both FIGS. 4 and 5, the outer cutting tube 152 has a closed end 164 and a plurality of outer ports 168 that receive tissue, such as ophthalmic tissue. The outer ports 168 are in fluid communication with an inner channel 170 of the outer cutting tube 152. In the exemplary embodiment shown, the outer cutting tube 152 includes four ports evenly spaced about the circumference of the outer tube 154. However, different numbers of ports may be used. Conventional systems employ a single port on a single side. However, multiple ports may allow a surgeon to perform surgeries in a more efficient manner because the surgeon need not rotate the vitrectomy device to align the port in a desired radial direction. In the example shown in FIGS. 4 and 5, the ports 168 are oval shaped and are configured to cooperate with the inner cutting tube 154 to cut tissue during an ophthalmic surgery. In some embodiments, the distal and proximal edges of the ports 168 are sharpened to aid in the cutting of the vitreous. The inner distance from the distal most edge of the ports 168 to the proximal facing wall of the closed end 164 may be a distance D.

Figure 6:
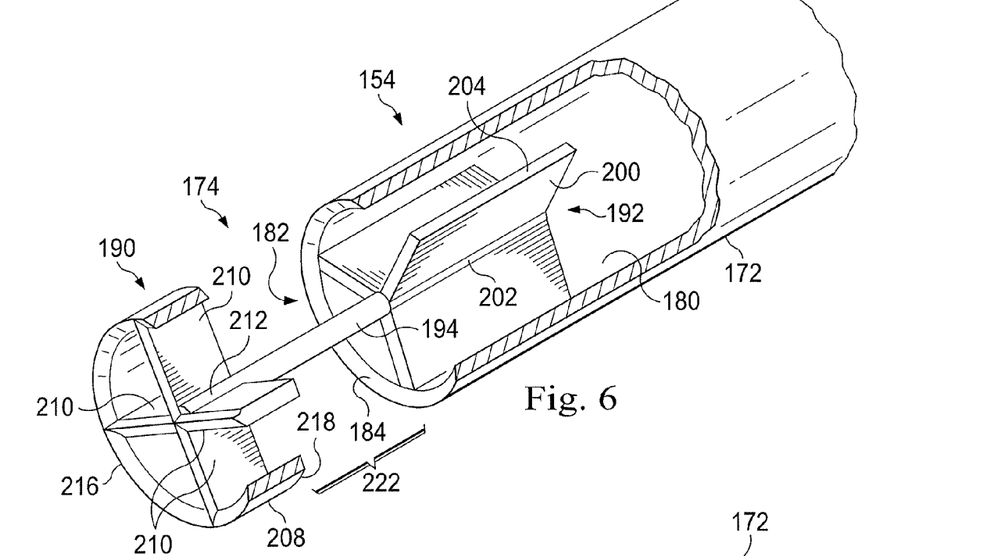
FIG. 6 is an illustration of an exemplary inner cutting tube in partial cross-section consistent with the principles and teachings described herein.

FIGS. 4 and 6 show the inner cutting member 154 in greater detail. FIG. 4 shows a side view of the inner cutting member 154 disposed within the sectioned outer cutting member 152. FIG. 6 shows a partial cross-sectional view of the cutting member 154.

The inner cutting tube 154 has a main tube 172 forming proximal portion and has a cutting element or cutting head 174. The main tube 172 is a cylindrical tube having an inner bore 180 and an open end 182. In this embodiment, the open end 182 includes a tapered leading edge 184 on its inner diameter. This facilitates the passage of tissue, as is explained further below. The inner bore 180 is in fluid communication with an aspiration line (not shown) that connects to a vacuum pressure that pulls tissue into the plurality of outer ports 168 when the inner cutting tube 154 is located away from the ports 168. The inner cutting tube 154 moves within the inner channel 170 of the outer cutting tube 152 in a cyclic motion to drive the cutting head 174 to cut tissue that is pulled into the outer ports 168 by the aspiration system. The ophthalmic tissue received by the outer ports 168 is preferably vitreous or membranes.

The cutting head 174 includes an anterior portion 190 and a posterior portion 192. These portions 190, 192 are spaced apart from each other and are rigidly secured together by a connecting portion 194, which in this embodiment is disclosed as a centrally disposed shaft.

The posterior portion 192 is disposed within the inner bore 180 of the main tube 172 and includes a plurality of cross-blades 200. These cross-blades 200 radially extend from a central intersection 202. The cross-blades 200 are sized so that their outer-facing edges 204 engage or connect to the interior of the inner bore 180 of the main tube 172, holding the cutting head 174 in place. These may be secured in place using welding, brazing, cements, or adhesives, friction fits, or other methods. In the embodiment shown, the cross-blades 200 of the posterior portion 192 of the cutting head 174 extend a sufficient length into the main tube 172 to anchor the cutting head 174 against displacement from the main tube 172 during the cutting cycle. Because the exemplary posterior portion 192 includes three radially extending cross-blades, the inner bore 180 of the main tube 172 is divided into three passages, each forming about a third of the area of the main tube 172. While shown with three cross-blades, other embodiments include two cross blades, while yet others include four or more.

The anterior portion 190 is spaced from the posterior portion 192 and from the open end 182 of the main tube 172. It includes an outer cutting blade 208 and anterior radial cross-blades 210 that converge at an intersection 212. The outer cutting blade 208 is a cylindrically shaped cutting blade having an outer diameter that substantially matches the outer diameter of the main tube 172. As such, it is configured to also slide within the inner bore 170 of the outer cutting tube 152. The outer cutting blade 208 includes a distal cutting edge 216 and a proximal cutting edge 218 separated by body having a length L. In some embodiments, the distal and proximal cutting edges 216, 218 are tapered or sharpened on their inner diameters in order to cleanly cut vitreous with a minimal of tissue shearing. This may reduce trauma to the vitreous remaining in the eye.

These anterior cross-blades 210 support or carry the outer cutting blade 208 and radially extend from the central intersection 212. Like the cross-blades 200, the cross-blades 210 are sized so that their outer-facing edges engage or connect to the interior of the outer cutting blade 208. In the embodiment shown, the cross-blades 200 extend the length L of the outer cutting blade 208; however, in other embodiments, the cross-blades do not have the same length as the outer cutting blade 208.

In the example shown in FIG. 6, the anterior portion 190 includes four radially extending cross-blades 210, which divides an inner bore formed by the outer cutting blade 208 into four passages, each forming about a quarter of the area of the inner diameter of the outer cutting tube 208. Accordingly, the area of each of the four passages is smaller than the area of each of the three passages formed by the posterior portion 192. These anterior cross-blades 210 therefore, may cut tissue, such as vitreous into segments small enough to easily pass beyond the posterior cross-blades 200 into the inner bore 180 of the main tube 172. In the embodiment shown, the main tube 172 and the outer cutting blade 208 have substantially the same inner diameter and substantially the same outer diameter. While shown with four anterior cross-blades 210, other embodiments include two or three cross blades, while yet others include five or more. In the embodiment shown, each of the cross-blades may include a sharpened leading surface on one or both edges to contribute to cutting the vitreous into small segments for easy aspiration.

The connecting portion 194 extends between and connects the intersection 202 and the intersection 212. In this embodiment, it extends along the central axis of the inner cutting tube 154. Other embodiments have two or more connecting portions that secure the anterior portion with the cutting blade 208 to the main tube 172.

The area between the anterior and posterior portions 190, 192, is referred to herein as the posterior cavity 222. In the embodiment shown, the posterior cavity 222 has a longitudinal length greater than the longitudinal length of the ports 168. Accordingly, tissue may enter the ports 168 into the posterior cavity 222 unimpeded when the posterior cavity is aligned with the ports 168. In other embodiments, however, the posterior cavity 168 has a longitudinal length smaller than the longitudinal length of the ports 168. In these embodiments, the full length of the port 168 may not be open to receive tissue at the same time.

Figure 7A:
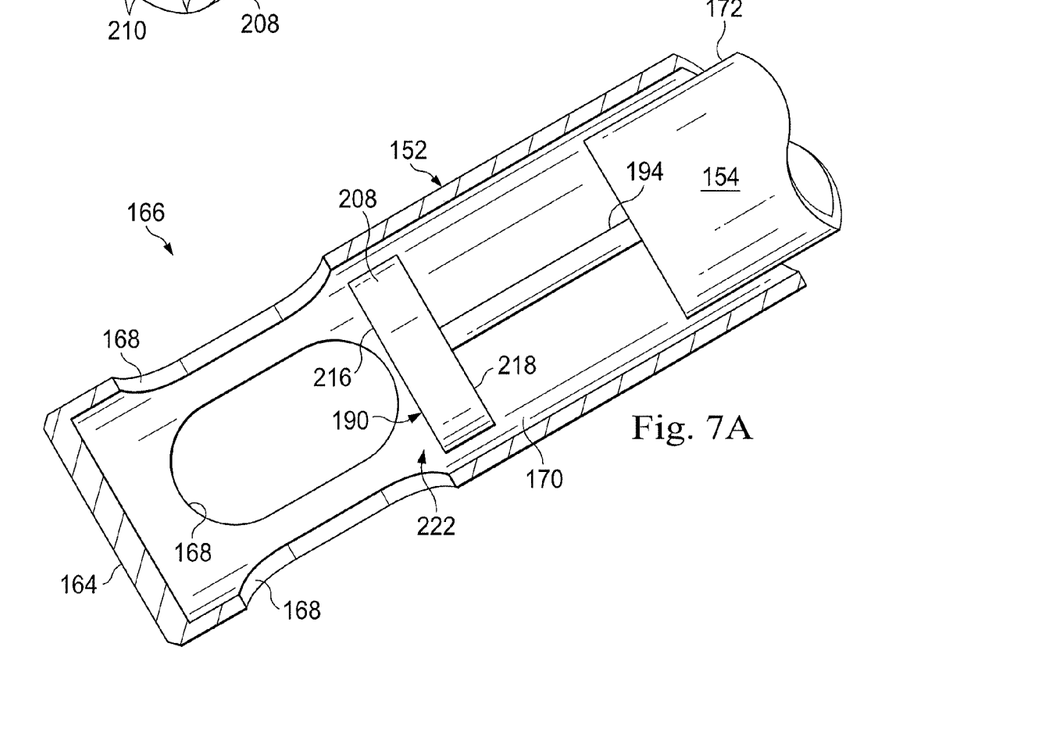
FIGS. 7A-7D are illustrations showing the inner and outer cutting tubes in partial cross-section and in different positions during a cutting cycle.

FIGS. 7A-7D show a cutting cycle of the vitrectomy cutter 150. FIG. 7A represents the portion of a cutting cycle when the inner cutting tube 172 is in the proximal position. In this position, the ports 168 are open, and vacuum pressure in the inner cutting tube 154 pulls tissue into the ports 168 and into the inner channel 170 of the outer cutting tube 152.

Figure 7B:
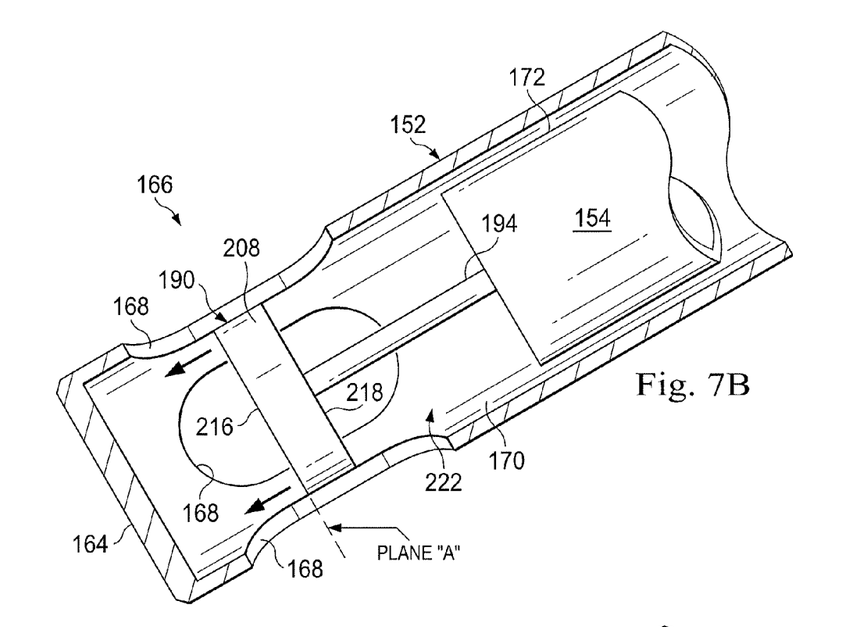
Figure 7C:
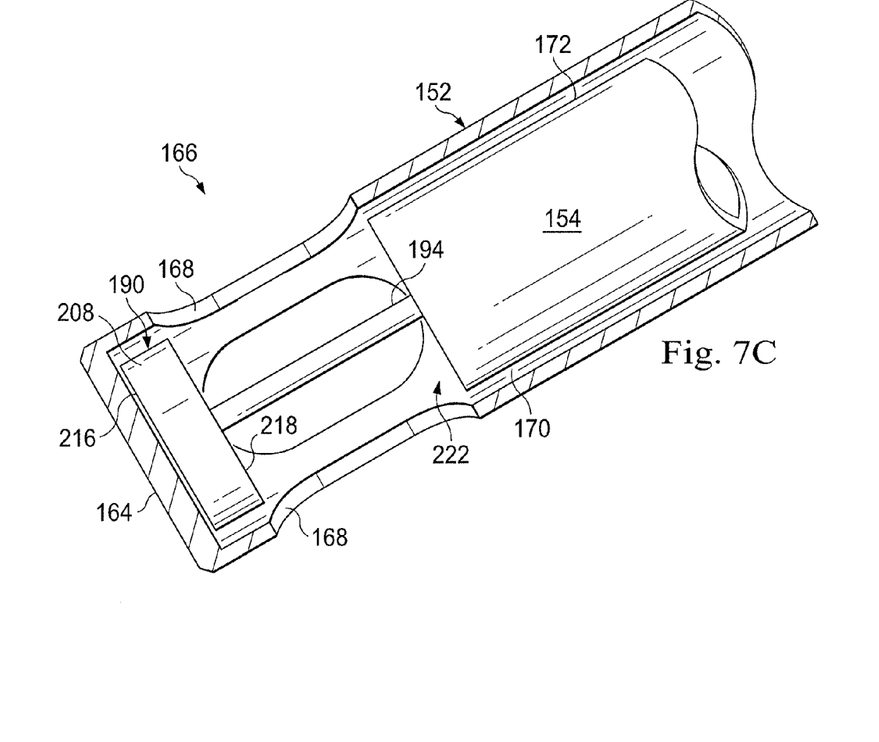

As shown in FIG. 7B, inner cutting tube 154, including the outer cutting blade 208 on the anterior portion of the cutting tube 154, travels distally toward distal end 164 of the outer cutting tube. As it moves, the distal cutting edge 216 cuts vitreous tissue that has entered the ports 168, severing the tissue within the inner channel 170. The severed tissue is pulled through the inner bore 180 of the inner cutting tube 154 by the aspiration system. At the same time, the vacuum pressure from the aspiration system continues to pull tissue into the ports 168 and into the inner channel 180. The inner cutting tube 154 moves distally until the outer cutting blade 208 is beyond the ports 168, as shown in FIG. 7C. At this point, the posterior cavity 222 is aligned with the ports 168 and the tissue is entering through the ports 168 and into the posterior cavity 222 formed between the anterior portion and the posterior portion of the cutting head 174. In some exemplary embodiments, the distance D (FIG. 4) showing the distance between the distal most edge of the ports 168 and the end 164 of the outer cutting tube is equal to or greater than the length L (FIG. 4) of the outer cutting blade 208. Accordingly, the outer cutting blade 208 can entirely pass beyond the ports 168 to permit vitreous to enter unimpeded.

Figure 7D:
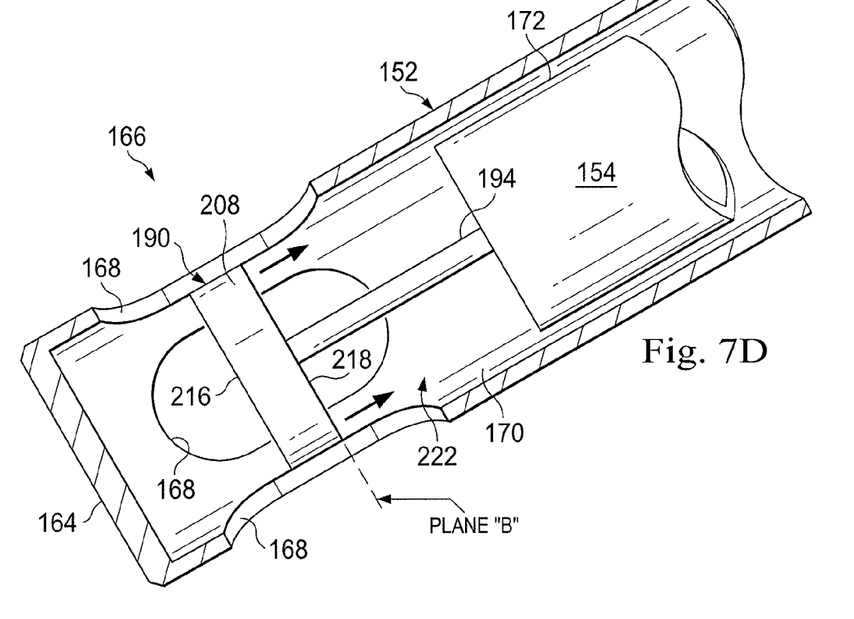

As shown in FIG. 7D, the inner cutting tube 154 then moves in the proximal direction, drawing the outer cutting blade 208 in the proximal direction. As the outer cutting blade 208 moves in the proximal direction, the proximal cutting edge 218 cuts vitreous tissue that has entered the posterior cavity 222 through the ports 168, severing the tissue within the inner channel 170. The severed tissue is pulled through the inner bore 180 of the inner cutting tube 154 by the aspiration system, and the inner cutting tube 154 returns to the position shown in FIG. 7A.

Here, the tissue cut by the anterior portion 190 of the cutting head 174 may be diced into small segments by the anterior cross-blades 210. Since the segments defined by the area between cross-blades 210 in the anterior portion 190 is smaller than the segments defined by the area between cross-blades 200 in the posterior portion 192, tissue segments may more easily aspirate past the posterior cross-blades 200. Any tissue that is too large to pass the posterior cross-blades 200 may be further severed by the cross-blades 200.

Because the cutting action occurs as the inner blade moves in both the proximal and the distal directions, the cutting blade performs a dual-action cutting cycle. This may double the cut rate of the vitrectomy probe. For example, while still operating the motor of the vitrectomy probe 112 at 10000 cycles/min., the effective cut rate is 20000 cycles/min since each cycle provides both an anterior cut and a posterior cut.

With reference now to both FIGS. 3 and 4, the inner cutting tube 154 is driven by air pressure directed on opposing sides of the diaphragm 156. In one example of operation, if air pressure is increased at the first port 140, the diaphragm 156 will move distally, displacing the inner cutting tube 154 relative to the outer cutting tube 152, thereby moving the cutting head 174 in the distal direction, and cutting tissue with the distal cutting edge 216. This cuts any vitreous material which may have been aspirated into the tissue-receiving outer port 168 and aligns the posterior cavity 222 with the ports 168. Venting the pressure at the first port 140 and increasing the pressure at the second port 214 moves the diaphragm 156 proximally, moving the outer cutting blade 208 in the proximal direction, cutting any vitreous material which may have entered into the posterior cavity. Its worth noting that other embodiments include alternative probe actuators. For example, some embodiments include a piston motor in place of a diaphragm. In this type of embodiment, the cutter 150 is arranged so that movement of the piston also moves the inner cutting tube 154 of the cutter 150. Yet other embodiments include other types of pneumatic or electric motors that drive the inner cutting tube 154.

Returning to FIG. 2, in the example shown, the vitrectomy probe system's pneumatic driver 122 is a standard four-way on-off valve. As is commonly known, the pneumatic driver 122 has a solenoid that operates to move the driver to one of the two on-off positions depicted in the example of FIG. 2. Here, the pneumatic driver 122 is in a position to provide pneumatic pressure to the first port 140, and to vent pneumatic pressure from the second port 142. In this position, pneumatic pressure can pass from the pressure source 120, through the on-off pneumatic driver 122, and to the first port 140 where the pneumatic pressure provides pneumatic power to the vitrectomy probe. At the same time, pneumatic pressure at the second port 142 can pass through the on-off pneumatic driver 122 to the muffler 124 where it is exhausted to the atmosphere. In the other position, the on-off pneumatic driver 122 allows pneumatic pressure to pass from the pressure source 120 to the second port 142 where the pneumatic pressure provides pneumatic power to the vitrectomy probe 112. At the same time, pneumatic pressure at the first port 140 can vent through the on-off pneumatic driver 122 to the muffler 124 where it is exhausted to the atmosphere. The on-off pneumatic driver is configured to receive operating signals from the controller 126 as further described below.

In operation, pneumatic pressure is directed alternately from the source 120 to the first and second ports 140, 142 to operate the vitrectomy probe 112. The on-off pneumatic driver 122 alternates between its two positions very rapidly to alternatingly provide pneumatic pressure to the first and second ports 140, 142.

Although shown with a single pneumatic driver 122, other embodiments include two pneumatic drivers, one associated with each of the two ports 140, 142. These embodiments operate similar to the manner described, with the drivers being configured to independently receive operating signals from the controller 126. Yet other arrangements are contemplated.

It is worth noting that the multiple ports on the outer cutting tube 152 may be used independently of the cutting head 174 on the inner cutting tube 154. Likewise, the dual cutting edges on the inner cutting tube 154 may be used independently of the multiple ports on the outer cutting tube 152.

Figure 8:
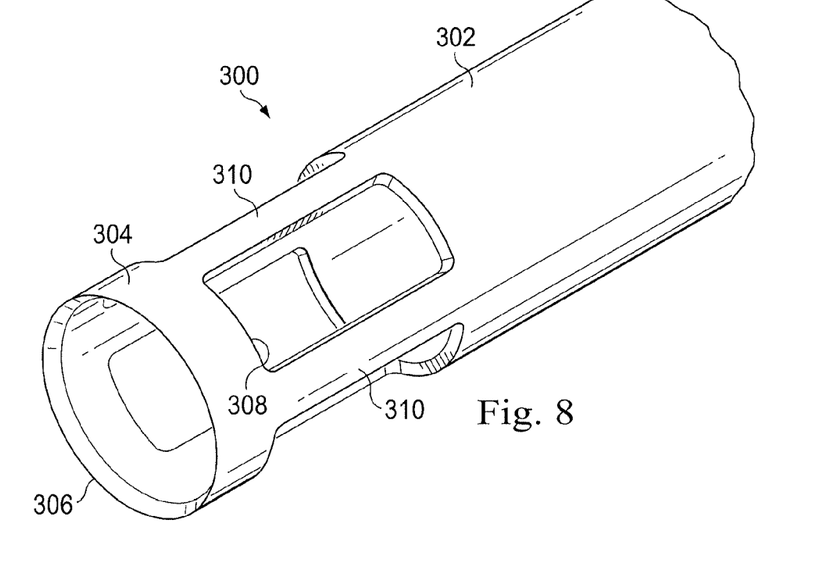
FIG. 8 is an illustration of an exemplary inner cutting tube consistent with the principles and teachings described herein.

FIG. 8 shows another embodiment of an inner cutting tube, referenced herein by the numeral 300. The inner cutting tube 300 is arranged to cooperate with the outer cutting tube 152 and includes a main tube 302 and a cutting head 304 with a cutting blade having a distal cutting edge 306 and a proximal cutting edge 308. In this embodiment, however, the connecting portion is not a centrally disposed shaft as in the embodiment of FIG. 4, but instead is a plurality of extending supports 310 that extend from the main tube 302 to the cutting head 304 and define a posterior cavity 312 therebetween. In use, the extending supports 310 align between the ports 168 in the outer cutting tube 152 so that the openings forming the posterior cavity 312 are aligned with the ports 168. As such the extending supports 310 do not interfere with or block the ports 168.

In one embodiment, the posterior cavity 312 is formed between the main tube and the cutting head 304 and may have an axial length equal to or greater than the ports 168 or may have an axial length less than that of the ports 168. In one embodiment, the cutting head includes anterior cross-blades (not shown in FIG. 8) as discussed above.

The systems, devices, and method described herein may improve surgical outcome by increasing cut rates and aspiration rates.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

We claim:

1. A vitrectomy probe, comprising:
   a hand-graspable body;
   an external tube extending from the hand-graspable body and sized to penetrate an eye of a patient during an ocular surgery, the external tube having a closed end, the external tube having a port sized to receive vitreous of the eye;
   an internal tube having a first cutting edge facing in a proximal direction and a second cutting edge facing in a distal direction, the internal tube being disposed within the external tube so that the first cutting edge oscillates across the port of the external tube to cut tissue in the port with the first cutting edge when the internal tube moves in the proximal direction and to cut tissue in the port with the second cutting edge when the internal tube moves in the distal direction; and a motor that drives the internal tube in a reciprocating motion relative to the external tube, wherein the internal tube comprises a distal portion and a proximal portion, the distal portion comprising the first cutting edge facing the proximal portion and comprising the second cutting edge facing in the distal direction, wherein the distal portion includes a first open end and a plurality of cross-blades extending across the first open end.

2. The vitrectomy probe of claim 1, wherein the proximal portion includes a second open end and a plurality of cross-blades extending across the second open end.

3. The vitrectomy probe of claim 2, wherein the distal portion includes a higher number of cross-blades extending across the first open end than a number of cross-blades extending across the second open end.

4. A vitrectomy probe, comprising:
a hand-graspable body;
an external tube extending from the body and sized to penetrate an eye of a patient, the external tube having a closed end, the external tube having a plurality of ports sized to receive vitreous of the eye;
an internal tube disposed within and axially slidable relative to the external tube, the internal tube having a first cutting edge facing in a distal direction, the first cutting edge being formed along an entire circumference of the internal tube, the internal tube being disposed within the external tube so that the first cutting edge oscillates across the port of the external tube to cut tissue in the plurality of ports with the first cutting edge when the internal tube moves in the distal direction, the internal tube including a second cutting edge facing in a proximal direction; and
a motor to drive the internal tube in a reciprocating motion, wherein the internal tube is disposed within the external tube so that the second cutting edge oscillates across the plurality of ports of the external tube to cut tissue in the plurality of ports with the second cutting edge when the internal tube moves in the proximal direction, wherein the internal tube comprises a distal portion and a proximal portion, the distal portion comprising the second cutting edge facing the proximal portion and comprising the first cutting edge facing in the distal direction, wherein the distal portion is rigidly fixed to and spaced apart from the proximal portion by a plurality of extending supports.

5. A vitrectomy probe, comprising:
a hand-graspable body;
an external tube extending from the hand-graspable body and sized to penetrate an eye of a patient during an ocular surgery, the external tube having a closed end, the external tube having a port sized to receive vitreous of the eye;
an internal tube having a first cutting edge facing in a proximal direction and a second cutting edge facing in a distal direction, the first cutting edge being formed along an entire circumference of the internal tube, the internal tube being disposed within the external tube so that the first cutting edge oscillates across the port of the external tube to cut tissue in the port with the first cutting edge when the internal tube moves in the proximal direction and to cut tissue in the port with the second cutting edge when the internal tube moves in the distal direction; and
a motor that drives the internal tube in a reciprocating motion relative to the external tube, wherein the internal tube comprises a distal portion and a proximal portion, the distal portion comprising the first cutting edge facing the proximal portion and comprising the second cutting edge facing in the distal direction, wherein the internal tube comprises an open end and a plurality of cross-blades extending across the open end.

6. A vitrectomy probe, comprising:
a hand-graspable body,
an external tube extending from the hand-graspable body and sized to penetrate an eye of a patient during an ocular surgery, the external tube having a closed end, the external tube having a port sized to receive vitreous of the eye;
an internal tube having a first cutting edge facing in a proximal direction and a second cutting edge facing in a distal direction, the first cutting edge being formed along an entire circumference of the internal tube, the internal tube being disposed within the external tube so that the first cutting edge oscillates across the port of the external tube to cut tissue in the port with the first cutting edge when the internal tube moves in the proximal direction and to cut tissue in the port with the second cutting edge when the internal tube moves in the distal direction; and
a motor that drives the internal tube in a reciprocating motion relative to the external tube, wherein the internal tube comprises a distal portion and a proximal portion, the distal portion comprising the first cutting edge facing the proximal portion and comprising the second cutting edge facing in the distal direction, wherein the distal portion is rigidly fixed to and spaced apart from the proximal portion by a plurality of extending supports.

* * * * *